United States Patent [19]
Beaty et al.

[11] 4,183,973
[45] Jan. 15, 1980

[54] CONTROL SYSTEM FOR A SLIDE CENTRIFUGE

[75] Inventors: Robert C. Beaty, Raleigh, N.C.; Gerald R. Mansfield, Painted Post, N.Y.

[73] Assignee: Corning Glass Works, Corning, N.Y.

[21] Appl. No.: 895,595

[22] Filed: Apr. 12, 1978

[51] Int. Cl.$^2$ .................. G01N 21/00; G01N 21/24
[52] U.S. Cl. ........................................ 427/2; 424/3; 118/6; 356/36; 356/39; 356/197
[58] Field of Search .................. 427/2; 424/3; 118/6, 118/51; 356/36, 197, 39

[56] References Cited
U.S. PATENT DOCUMENTS

| | | | |
|---|---|---|---|
| 3,827,805 | 8/1974 | Mansfield | 356/36 |
| 4,055,076 | 10/1977 | Tropea | 356/197 |

*Primary Examiner*—Sam Silverberg
*Attorney, Agent, or Firm*—Walter S. Zebrowski; William J. Simmons, Jr.; Richard E. Kurtz

[57] ABSTRACT

A control system for a slide centrifuge includes a ratio checking circuit which produces a signal when the ratio between the light passing through the slide and the rate of change of this light passes through a predetermined critical value. When this ratio passes through the critical value, spinning is stopped. This effectively stops spinning when the rate of reduction of blood cell density on the slide slows, thereby producing better slides for clinical analysis.

2 Claims, 1 Drawing Figure

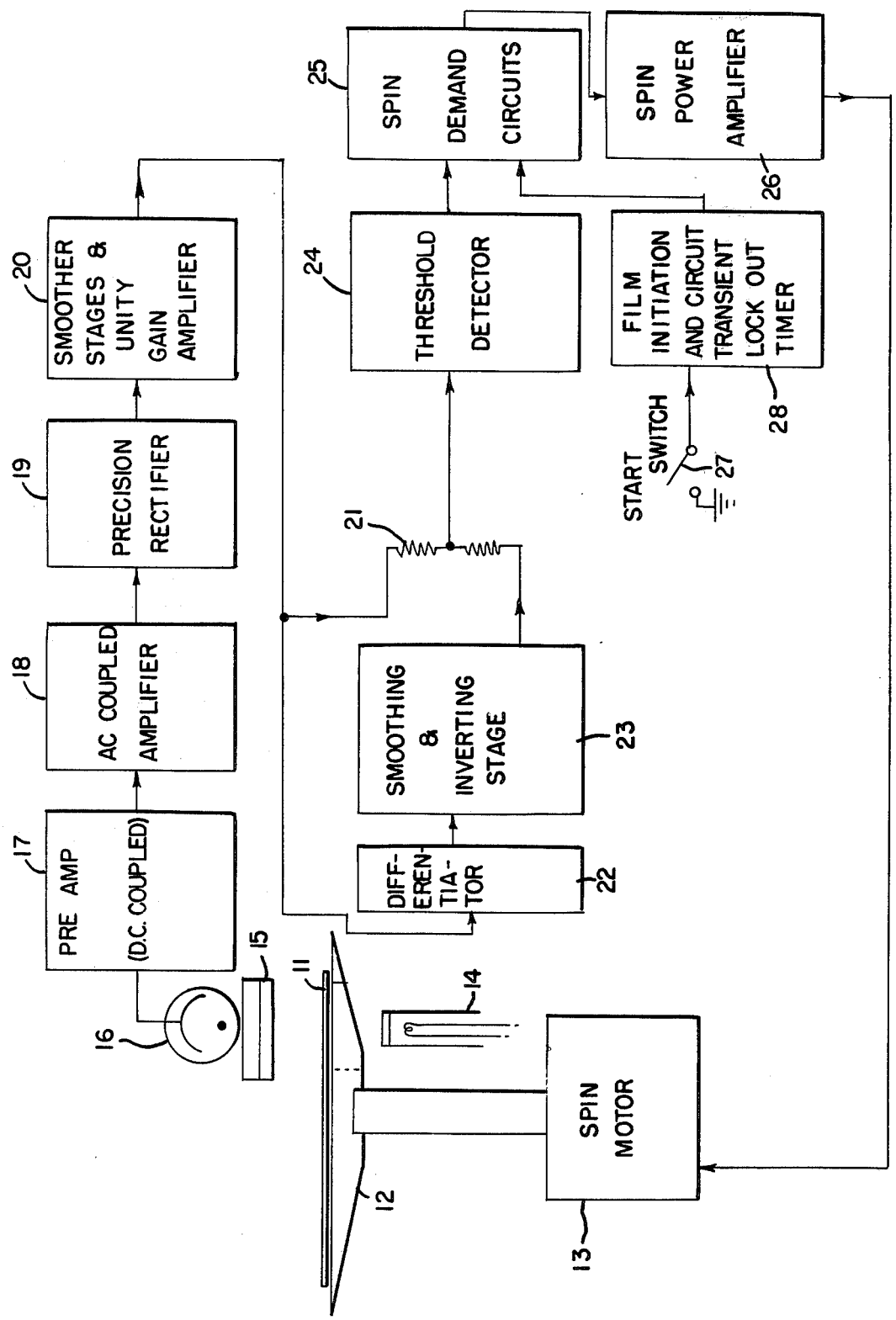

CONTROL SYSTEM FOR A SLIDE CENTRIFUGE

BACKGROUND OF THE INVENTION

This invention relates to control systems for slide centrifuges and more particularly to methods of and apparatus for producing blood smeared slides for clinical analysis.

Examination of cell morphology yields important medical data. Frequently, cell samples are obtained in the form of cells suspended in a liquid. A particular case is the analysis of blood samples. The blood is smeared on a laboratory slide and the smear is stained. By counting the leukocytes on the stained smear, laboratory technicians perform what is referred to as a white blood cell differential count. Recently, the analysis of blood smeared slides has been automated. In automated analysis, it is particularly important to consistently produce a slide with a uniform monolayer of blood cells.

U.S. Pat. No. 3,577,267 Preston et al. and U.S. Pat. No. 3,705,048 Staunton describe centrifuges which can be used to prepare blood slides. However, the problem is that the spinning time must be changed for different blood smears because blood of different hematocrits and other blood properties requires different spinning times to produce a uniform monolayer.

One solution to this problem is disclosed in U.S. Pat. No. 3,827,805, Mansfield et al wherein the time of spinning is controlled by a signal derived from photodetectors which detect the ratio of direct and scattered light passing through the spinning slide. This control arrangement does not directly measure the separation of the cells. Occasionally, the optical and physical properties of the blood are such as to cause unduly short or unduly long spin times, causing slides to be under or overspun. Moreover, it is sometimes difficult to align the optical systems which detect the ratio of direct and scattered light.

SUMMARY OF THE INVENTION

In accordance with this invention the blood cell density on a spinning slide is monitored as spin proceeds and spinning is stopped when the rate of reduction of the cell density slows.

The present invention simplifies the optics and circuitry of the spin control system by providing a single optical channel in which the spreading of the blood cells is sensed by light absorption. Blood cells absorb light of 415 nanometer wavelengths. A thin monolayer of blood cells is essentially transparent but there is absorption of 415 nanometer light and this absorption is proportioned to the number of cells in the path.

In carrying out the invention a photodetector senses the amount of light passing through the spinning slide. The output of the photodetector is amplified, detected, differentiated, and inverted t produce a signal representing the rate of change of light passing through the slide but of opposite polarity to the signal representing the light transmitted tnrough the slide. The rate of change signal is applied to one end of a potentiometer and the signal representing transmitted light is applied to the other end of the potentiometer. A signal at a tap on the potentiometer will have zero potential when the ratio between these two signals has a predetermined value. When this ratio passes through the predetermined value, spinning is stopped. Sensing the predetermined ratio is independent of the strength of the light source and many circuit parameters which are not related to blood cell spreading. Because of this, uniform monolayers are produced reliably.

In accordance with the invention, the density of the blood cells is measured with 415 nanometer wavelength light. Transmission of 415 nanometer light steadily increases as the red blood cells are spread further apart. As the film thickness decreases, the spreading of the red cells slows and stops. By stopping spinning somewhat before the cells stop spreading, good, easily analyzed, slides are produced. The control system of the present invention stops the spinning when the spreading of the blood cells slows.

The foregoing and other objects, features and advantages of the invention will be better understood from the following more detailed description and appended claims.

DESCRITPION OF THE DRAWINGS

The FIGURE shows a block diagram of the control system of this invention.

DESCRIPTION OF THE PREFERRED EMBODIMENT

A slide 11 is mounted on a platen 12 which is rotated by motor 13. Slide 11 has a quantity of blood thereon which is centrifuged into a monolayer. The control system of this invention controls the time of spinning.

A filament light source 14 is mounted in a protective housing. Light source 14 is powered by a regulated, smooth, direct potential. Platen 12 has holes therein so that light from source 14 intermittently passes through slide 11 ad the blood film thereon. Light source 14 emits a broad spectrum of light including light of 415 nanometer wavelength.

A light filter 15 includes two thicknesses of Corning color filter glass CS5-58 which passes 415 nanometer light to the photodetector 16 which, in this example, is a vacuum photo diode. Whereas the scattered light detection system of the aforementioned Mansfield et al patent detects light of any wavelength, in the present invention it is important to use a wavelength at which absorption occurs. It is possible to use light of wavelengths other than 415 nanometers. Some absorption of light with wavelengths in the range of 500–600 nanometers has been observed.

The output of the photodetector 16 is amplified by amplifiers 17 and 18. The signal is applied to the precision rectifier 19 and smoother stages 20 which produce a first signal representative of the 415 nanometer light passing through the blood smear. This first signal is applied to one end of the potentiometer 21 which is part of the ratio checking circuit. This first signal is also applied to a differentiator 22. The differentiated signal is smoothed and inverted in the stage 23 to produce a second signal representing the negative of the rate of change of light passing through the blood smear. This signal is a measure of the absorption of light passing through the slide and is correlated with the density of blood cells in the smear. The second signal is applied to the second end of the potentiometer 21. When the output at the tap of potentiometer 21 is zero, the ratio between the first and second signals is at the predetermined value. When the output of potentiometer 21 passes through zero potential, the threshold 24 stops the spinning. This stops the spinning when the rate of change of light absorption reaches a predetermined level. The time at which the output at the tap of potentiometer 21 reaches zero is not affected by lamp intensity, photo diode sensitivity, preamplifier and AC coupled amplifier gains because these factors affect both the first and second signal applied to the potentiometer in the same proportion.

The output of the threshold detector controls the spin demand circuits 25 and the spin power amplifier 26 which start and stop the spin motor 13. Circuits 24, 25 and 26 may be similar to those shown in FIGS. 5 and 6 of U.S. Pat. No. 3,827,805. In that patent the spinning is stopped when the signals from the photocell reach a changing threshold. In the subject control system, spinning is stopped when the output at the tap of the potentiometer 21 passes through zero.

Spinning is started by closure of the switch 27. The lockout timer 28 is provided so that spurious signals occurring during initial blood film formation and transients due to the application of signals to the electronic system cannot cause premature spin shutdown. FIG. 5A of U.S. Pat. No. 3,827,805 shows a lockout circuit which is suitable for use.

One of the first and second signals is inverted. As shown in the figure, the second signal is inverted. Alternatively, the first signal can be inverted. However, it is usually convenient to invert the second signal because the inversion can be produced in conjunction with the differentiation.

Other modifications are within the true spirit and scope of the invention. The appended claims are intended to cover all such modifications.

What is claimed is:

1. A method of producing a slide having a monolayer of blood cells thereon comprising:
   placing a blood sample on said slide,
   spinning said slide in a centrifuge,
   measuring the absorption of light passing through said slide, the intensity of said light being correlated with the density of blood cells in said film, determining the ratio between the measured amount of light absorbed and the rate of change of the measured amount of absorbed light, and
   stopping the spinning when said ratio reaches a predetermined level.

2. The method recited in claim 1 wherein absorption of light having a wavelength of approximately 415 nanometers is measured.

* * * * *

UNITED STATES PATENT AND TRADEMARK OFFICE
CERTIFICATE OF CORRECTION

PATENT NO. : 4,183,973
DATED : January 15, 1980
INVENTOR(S) : Robert C. Beaty - Gerald R. Mansfield It is certified that error appears in the above-identified patent and that said Letters Patent are hereby corrected as shown below:

Column 1, line 56, "t" should be -- to --.

Column 1, line 59, "tnrough" should be -- through --.

Column 2, line 32, "ad" should be -- and --.

Column 2, line 65, "24" should be -- detector 24 --.

Signed and Sealed this

Thirteenth Day of May 1980

[SEAL]

Attest:

SIDNEY A. DIAMOND

Attesting Officer   Commissioner of Patents and Trademarks